United States Patent
Witt et al.

(10) Patent No.: US 9,803,627 B2
(45) Date of Patent: Oct. 31, 2017

(54) SERIAL TYPE PUMP COMPRISING A HEAT EXCHANGER

(75) Inventors: Klaus Witt, Keltern (DE); Konstantin Shoykhet, Waldbronn (DE); Philip Herzog, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 342 days.

(21) Appl. No.: 12/763,806

(22) Filed: Apr. 20, 2010

(65) Prior Publication Data

US 2010/0299079 A1  Nov. 25, 2010

(30) Foreign Application Priority Data

May 20, 2009  (EP) .................................... 09158271

(51) Int. Cl.

| | | |
|---|---|---|
| *B01D 15/14* | (2006.01) | |
| *G01N 30/24* | (2006.01) | |
| *G01N 30/30* | (2006.01) | |
| *F04B 11/00* | (2006.01) | |
| *F04B 23/06* | (2006.01) | |
| *F04B 53/08* | (2006.01) | |

(52) U.S. Cl.
CPC .......... *F04B 23/06* (2013.01); *F04B 11/0075* (2013.01); *F04B 53/08* (2013.01);
(Continued)

(58) Field of Classification Search
CPC .... F04B 23/06; F04B 11/005; F04B 11/0075; F04B 53/08; F04B 2205/10;
(Continued)

(56) References Cited

U.S. PATENT DOCUMENTS

| | | |
|---|---|---|
| 2,590,341 A | 2/1946 | Nabholz |
| 2,580,341 A | 12/1951 | Aikman |
| | (Continued) | |

FOREIGN PATENT DOCUMENTS

| | | |
|---|---|---|
| GB | 276612 | 2/1928 |
| GB | 276612 A | 2/1928 |
| | (Continued) | |

OTHER PUBLICATIONS

European Search Report dated Oct. 2, 2009.
(Continued)

*Primary Examiner* — Joseph Drodge

(57) ABSTRACT

A pump unit comprises a primary piston pump, a secondary piston pump, and a flow path adapted for fluidically connecting in series the primary piston pump and the secondary piston pump. The pump unit's duty cycle comprises a delivery-and-fill phase, in which the primary piston pump supplies a flow of liquid to the secondary piston pump, and during the delivery-and-fill phase, the flow of liquid supplied by the primary piston pump is partly used for filling up the secondary piston pump and partly used for maintaining another flow of liquid dispensed across the secondary piston pump. The flow path comprises a heat exchanger, wherein liquid supplied by the primary piston pump passes through the heat exchanger before being supplied to the secondary piston pump. The heat exchanger is adapted for reducing a temperature difference between a temperature of liquid supplied to heat exchanger and a temperature of the secondary piston pump, in that the heat exchanger is kept at a temperature of the secondary piston pump, so that after having passed the heat exchanger, liquid supplied to the secondary piston pump has substantially the same temperature as the secondary piston pump itself.

8 Claims, 7 Drawing Sheets

(52) U.S. Cl.
CPC ..... *F04B 2205/10* (2013.01); *F04B 2205/112* (2013.01); *G01N 30/24* (2013.01); *G01N 30/30* (2013.01)

(58) Field of Classification Search
CPC .. F04B 2205/11; F04B 2205/13; F04B 23/04; F04B 25/00; F04B 25/005; F04B 25/02; F04B 11/00; F04B 11/075; F04B 39/00; F04B 39/0027; F04B 39/06; F04B 39/066; F04B 49/00; F04B 49/10; F04B 2201/02; F04B 2201/0201; F04B 2201/0202; F04B 2201/0801; F04B 2207/03; F04B 2207/043; F04B 11/0058; F04B 2205/112; F25B 2600/01; F25B 2600/13; F25B 2600/23; F25B 2700/21; F25B 2700/2103; G01N 30/04; G01N 30/24; G01N 30/26; G01N 30/28; G01N 30/30; G01N 30/3092; G01N 30/3046; G01N 30/32; G01N 30/324; G01N 30/326; G01N 30/02; G01N 203/322; G01N 203/324; G01N 203/326; B01D 15/08; B01D 15/10; B01D 15/12; B01D 15/14; B01D 15/18; B01D 19/00; B01D 19/0068; B01D 19/0073
USPC ............ 210/101, 137, 149, 175, 198.2, 258; 417/1, 2, 32, 53, 65, 244–246, 254, 207, 417/258, 259, 313, 426; 137/565.11, 137/565.3, 565.31, 565.32; 73/61.56; 96/105; 165/47, 132, 138, 287
See application file for complete search history.

(56) References Cited

U.S. PATENT DOCUMENTS

| | | | | |
|---|---|---|---|---|
| 2,586,899 | A * | 2/1952 | Yanikoski | 73/25.01 |
| 3,902,848 | A * | 9/1975 | Juvet et al. | 436/149 |
| 4,003,679 | A * | 1/1977 | McManigill | 417/246 |
| 4,406,158 | A * | 9/1983 | Allington | G01N 30/30 417/32 |
| 4,600,365 | A * | 7/1986 | Riggenmann | F04B 11/0066 417/246 |
| 4,624,625 | A * | 11/1986 | Schrenker | 417/20 |
| 4,820,129 | A * | 4/1989 | Magnussen, Jr. | F04B 11/0041 210/101 |
| 4,981,597 | A * | 1/1991 | Allington et al. | 210/656 |
| 5,167,837 | A * | 12/1992 | Snodgrass et al. | 210/767 |
| 5,634,779 | A * | 6/1997 | Eysymontt | F04B 9/1178 417/342 |
| 6,228,153 | B1 * | 5/2001 | Saitoh | 96/218 |
| 6,627,075 | B1 | 9/2003 | Weissgerber et al. | |
| 7,017,606 | B1 | 3/2006 | Sanders | |
| 8,158,004 | B2 * | 4/2012 | Miyazawa | B01D 15/40 210/198.2 |
| 2003/0190237 | A1 * | 10/2003 | Berger | F04B 11/0091 417/53 |
| 2004/0164013 | A1 * | 8/2004 | Takao et al. | 210/198.2 |
| 2006/0054543 | A1 * | 3/2006 | Petro et al. | 210/198.2 |
| 2010/0040483 | A1 * | 2/2010 | Berger et al. | 417/205 |
| 2010/0288027 | A1 * | 11/2010 | Ishii et al. | 73/61.56 |

FOREIGN PATENT DOCUMENTS

| | | |
|---|---|---|
| WO | 2006/017121 | 2/2006 |
| WO | WO2006017121 A2 | 2/2006 |
| WO | 2006/103133 | 10/2006 |
| WO | 2007/051469 | 5/2007 |

OTHER PUBLICATIONS

Office Action mailed Jun. 6, 2014 in Chinese Patent Application No. 201010154209.5.

Office Action dated Oct. 21, 2013 in Chinese Patent Application No. 201010154209.5.

* cited by examiner

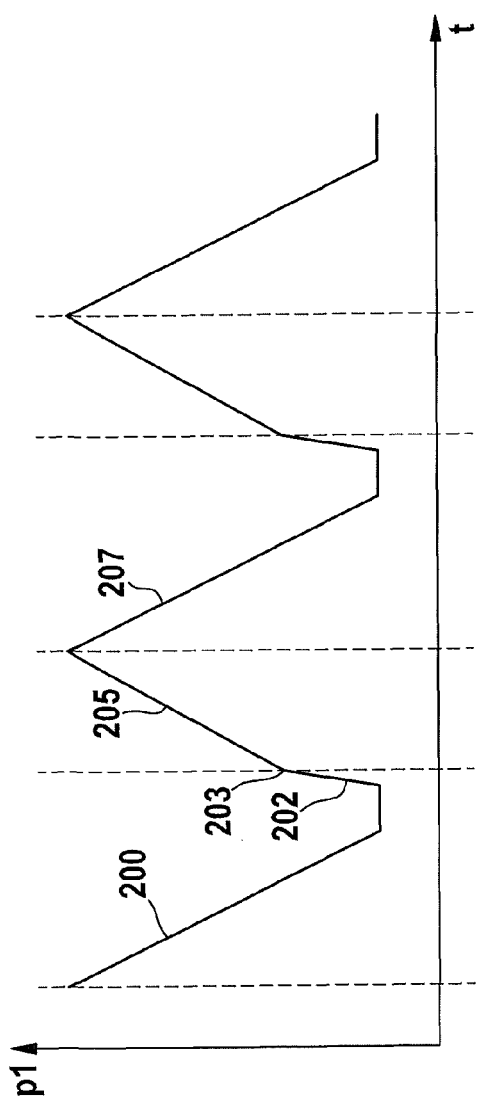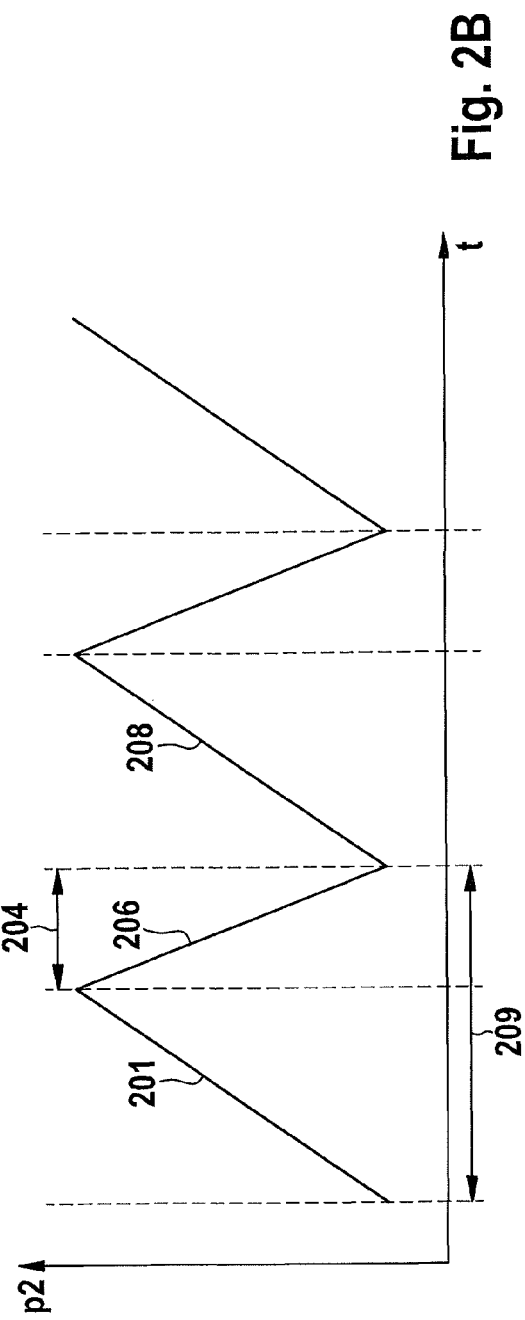

SERIAL TYPE PUMP COMPRISING A HEAT EXCHANGER

This application claims priority from European Patent Application, No. EP09158271.8 filed on 20 May 2009, which is incorporated by reference in its entirety.

The present invention relates to a pump unit, and to a fluid separation system for separating compound of a sample fluid in a mobile phase. The present invention further relates to a method of operating a pump unit comprising a primary piston pump fluidically connected in series with a secondary piston pump.

BACKGROUND

GB 276612 A and U.S. Pat. No. 2,580,341 A disclose serial pumps for gas compression with cooling of the gas between the pumps.

U.S. Pat. No. 6,627,075 B1 discloses preparing volume flows of liquid in an HPLC column.

International patent application WO 2006017121 describes a feedback control loop for a high pressure pump that modifies the accumulator velocity and pressure during solvent transfer. The accumulator velocity is adjusted to maintain the system pressure equal to the expected pressure to thereby eliminate the effect of the flow deficit created by a thermal effect.

International patent application WO 2006103133 A1 relates to a method for controlling movement of a piston in a metering device. The method comprises supplying a fluid by actuating the metering device's piston, wherein compression or expansion of the fluid causes corresponding temperature variations. The method further comprises superposing a corrective movement onto the piston movement, with the corrective movement at least partly compensating for at least one of thermal expansion and contraction of the fluid induced by the temperature variations.

SUMMARY

It is an object of the invention to provide an improved pump unit comprising a primary piston pump and a secondary piston pump fluidically connected in series.

A pump unit according to embodiments of the present invention comprises a primary piston pump, a secondary piston pump, and a flow path adapted for fluidically connecting in series the primary piston pump and the secondary piston pump. The flow path comprises a heat exchanger, wherein fluid supplied by the primary piston pump passes through the heat exchanger before being supplied to the secondary piston pump, the heat exchanger being adapted for reducing a temperature difference between the fluid's temperature and the secondary piston pump's temperature.

In pump units of the prior art, temperature variations have occurred in the flow of fluid supplied to the secondary piston pump. For example, during the primary piston pump's operation, the volume of fluid in the primary piston pump may be subjected to compression and expansion, and accordingly, the fluid may be heated up or cooled down. These temperature variations may cause corresponding volumetric changes resulting in disturbances in the flow of fluid supplied by the pump unit.

In prior art pump units, in dependence on the pump system's set-up, there may exist various different temperature relaxation processes for equilibrating temperature variations occurring in the system. In general, several different temperature relaxation processes having different time constants contribute to leveling out any temperature variations of the fluid. The time behavior of the overall temperature relaxation may depend on a plurality of different parameters including geometrical and material properties of the piston pumps and the fluid conduits, heat capacitances, thermal conductivities, especially of the fluid itself, etc. Hence, it has been difficult to understand the temperature relaxation processes in a given system.

By providing a heat exchanger in the flow path between the primary piston pump and the secondary piston pump, any kind of temperature variation in the flow of fluid is eliminated. When driving the fluid through the heat exchanger faster than the time constant of the natural cool-down, then the relaxation process is substantially governed by the timing of the actively driven process of delivering the fluid from the primary piston pump to the secondary piston pump. In the following, this process will be referred to as a deliver-and-fill phase. This way no matter what kind of temperature variation would occur upstream of the heat exchanger, the heat exchanger is adapted to enforce a well-defined temperature relaxation process. For example, the heat exchanger may bring the flow of fluid to a predefined temperature within the time given for the delivery-and-fill phase. Therefore, temperature relaxation variations that occur upstream of the heat exchanger do not affect those parts of the fluidic system that are located downstream of the heat exchanger.

A heat exchanger is capable of eliminating or reducing temperature variations that have occurred upstream of the heat exchanger. As a consequence, temperature-induced volumetric change variations are eliminated or reduced as well. Thus, the flow of fluid is stabilized, and a precisely metered flow is provided at the outlet of the pump unit.

According to a preferred embodiment, the heat exchanger is adapted for substantially bringing the fluid supplied by the primary piston pump to a predefined temperature before said fluid is supplied to the secondary piston pump. Thus, any temperature variations that have occurred upstream of the heat exchanger are eliminated during the delivery-and-fill phase and do not affect the system behavior downstream of the heat exchanger.

According to a preferred embodiment, the heat exchanger is adapted for substantially bringing the fluid supplied by the primary piston pump to the secondary piston pump's temperature. For example, the heat exchanger may be thermally coupled to the secondary piston pump. Thus, it is prevented that two fluids of different temperature are mixed in the secondary piston pump. Thus, any disturbances caused by mixing two fluids having different temperatures are avoided. In a preferred embodiment, after having passed the heat exchanger, fluid supplied to the secondary piston pump has substantially the same temperature as the secondary piston pump itself. Preferably, the heat exchanger is kept at a temperature of the secondary piston pump. Alternatively, the heat exchanger may e.g. be kept at a temperature which is sufficient even with limited thermal transfer efficiency to reach a temperature close to that of the secondary piston pump.

According to a preferred embodiment, the heat exchanger is adapted for enforcing a well-defined temperature relaxation of a flow of fluid supplied to the secondary piston pump.

According to a preferred embodiment, the pump unit comprises a thermostatted heating element adapted for keeping both the heat exchanger and the secondary piston pump at a predefined temperature. According to another preferred embodiment, the heat exchanger comprises a heat reservoir and a plurality of capillaries in thermal contact with the heat reservoir.

According to a preferred embodiment, the pump's duty cycle comprises a delivery-and-fill phase, in which the primary piston pump supplies a flow of fluid to the secondary piston pump.

In a preferred embodiment, during the delivery-and-fill phase, the flow of fluid supplied by the primary piston pump is partly used for filling up the secondary piston pump and partly used for maintaining another flow of fluid dispensed across the secondary piston pump. Thus, a continuous flow of fluid is maintained at the pump unit's outlet.

According to a preferred embodiment, during the delivery-and-fill phase, the flow of fluid supplied by the primary piston pump is conveyed through the heat exchanger. According to another preferred embodiment, the delivery-and-fill phase extends over less than 10% of the pump unit's duty cycle.

According to a preferred embodiment, the pump unit comprises a control unit adapted for controlling the piston movement of at least one of the primary piston pump and the secondary piston pump. According to another preferred embodiment, the pump unit comprises a control unit adapted for controlling the piston movement of at least one of the primary piston pump and the secondary piston pump, the control unit being adapted for superimposing at least one corrective movement onto the primary piston pump's piston movement, said at least one corrective movement being adapted for compensating volumetric effects that are due to temperature variations of the fluid.

According to a preferred embodiment, during a compression phase, before supplying a flow of fluid to the secondary piston pump, the primary piston pump is adapted for imposing a compression onto a volume of fluid contained in the primary piston pump to bring the volume of fluid to system pressure.

According to a preferred embodiment, during a compression phase, before supplying a flow of fluid to the secondary piston pump, the primary piston pump is adapted for imposing a compression onto a volume of fluid contained in the primary piston pump to bring the volume of fluid to system pressure, wherein the compression gives rise to a corresponding temperature increase of the volume of fluid, with the temperature increase causing a corresponding volume expansion of the volume of fluid contained in the primary piston pump.

According to a preferred embodiment, the pump unit comprises a control unit adapted for controlling the piston movement of at least one of the primary piston pump and the secondary piston pump, the control unit being adapted for superposing a first corrective movement onto the primary piston pump's piston movement, said first corrective movement being adapted for compensating volumetric effects related to a temperature increase caused by compressing a volume of fluid contained in the primary piston pump.

According to a preferred embodiment, during a compression phase, when the fluid contained in the primary piston pump is compressed to system pressure, a volumetric expansion related to a corresponding temperature increase is compensated for by decreasing a compression imposed onto a volume of fluid contained in the primary piston pump.

According to a preferred embodiment, the pump unit comprises a control unit adapted for controlling the piston movement of at least one of the primary piston pump and the secondary piston pump, the control unit being adapted for superposing a second corrective movement onto the primary piston pump's piston movement, said second corrective movement being adapted for compensating volumetric effects related to a temperature relaxation enforced by the heat exchanger.

According to a preferred embodiment, when a flow of fluid supplied by the primary piston pump passes through the heat exchanger, a time dependence of the temperature relaxation is enforced by a flow rate of the fluid passing through the heat exchanger.

According to a preferred embodiment, volumetric effects that are due to a temperature relaxation enforced by the heat exchanger are compensated for by superposing, as long as the flow of fluid passes through the heat exchanger, an additional velocity onto the primary piston pump's piston movement.

According to a preferred embodiment, as long as a flow of fluid passes through the heat exchanger, an additional velocity or profile is superposed onto the primary piston pump's piston movement.

A fluid separation system according to embodiments of the present invention is adapted for separating compounds of a sample fluid in a mobile phase. The fluid separation system comprises a mobile phase drive, preferably a pumping system, adapted to drive the mobile phase through the fluid separation system, said mobile phase drive comprising a pump unit as described above, and a separation unit, preferably a chromatographic column, adapted for separating compounds of the sample fluid in the mobile phase.

According to a preferred embodiment, the fluid separation system comprises at least one of: a sample injector adapted to introduce the sample fluid into the mobile phase, a detector adapted to detect separated compounds of the sample fluid, a collection unit adapted to collect separated compounds of the sample fluid, a data processing unit adapted to process data received from the fluid separation system, and a degassing apparatus for degassing the mobile phase.

According to embodiments of the present invention, a method of operating a pump unit is provided, the pump unit comprising a primary piston pump fluidically connected in series with a secondary piston pump. The method comprises supplying a flow of fluid from the primary piston pump to the secondary piston pump to refill the secondary piston pump with fluid, and passing the flow of fluid supplied by the primary piston pump through a heat exchanger, thereby reducing a temperature difference between the fluid's temperature and the secondary piston pump's temperature. At the same time, the flow of fluid may e.g. be provided to the system further downstream of the secondary piston pump.

According to a preferred embodiment, the method comprises superposing at least one corrective movement onto the primary piston pump's piston movement, said at least one corrective movement being adapted for compensating for volumetric effects related to temperature variations caused by compression or expansion of the fluid.

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied for controlling piston movement of the primary and the secondary piston pump.

BRIEF DESCRIPTION OF DRAWINGS

Other objects and many of the attendant advantages of embodiments of the present invention will be readily appreciated and become better understood by reference to the following more detailed description of embodiments in connection with the accompanied drawing(s). Features that are substantially or functionally equal or similar will be referred to by the same reference sign(s).

FIG. 2 depicts the piston positions of the primary piston pump and the secondary piston pump as a function of time;

DETAILED DESCRIPTION

Figure 1:
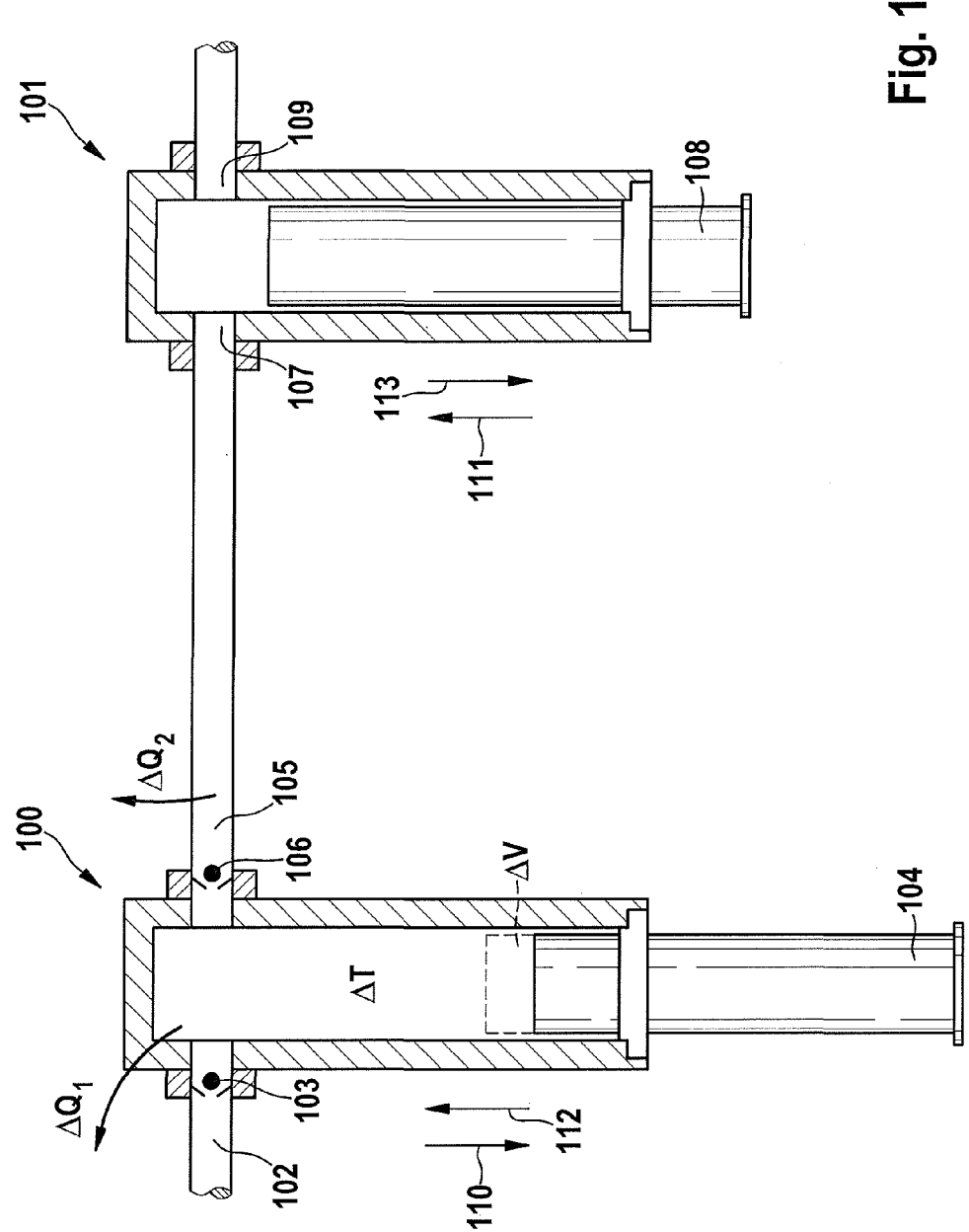
FIG. 1 shows a dual piston serial-type pump comprising a primary piston pump that is fluidically connected in series with a secondary piston pump.

FIG. 1A shows a dual piston serial-type pump comprising a primary piston pump 100 that is fluidically connected in series with a secondary piston pump 101. The primary piston pump 100 comprises an inlet 102 with an inlet valve 103, a piston 104 that reciprocates in the primary piston pump 100, and an outlet 105 with an outlet valve 106. The outlet 105 is fluidically connected with an inlet 107 of the secondary piston pump 101. The outlet valve 106 can be located anywhere along the connection tubing to the inlet 107. A piston 108 reciprocates in the secondary piston pump 101. The secondary piston pump 101 further comprises an outlet 109 for delivering a flow of fluid.

During an intake phase of the primary piston pump 100, the inlet valve 103 is open, the outlet valve 106 is shut, and the piston 104 moves downwards, as indicated by arrow 110. Via the inlet 102, fluid at or close to atmospheric pressure is drawn into the pump chamber of the primary piston pump 100. In the meantime, the piston 108 of the secondary piston pump 101 moves upwards, as indicated by arrow 111, and at the outlet 109, fluid at system pressure is dispensed.

Then, during a subsequent compression phase of the primary piston pump 100, the piston 104 starts moving upwards, as indicated by arrow 112. Both the inlet valve 103 and the outlet valve 106 are shut, and the fluid contained in the pump chamber of the primary piston pump 100 is compressed to system pressure. System pressure may for example be in the range of several hundred bar or even more than thousand bar. The compression of the fluid causes a temperature increase $\Delta T$ of the fluid in the pump chamber, and the temperature increase $\Delta T$ may in turn cause a volume expansion and/or a pressure increase of the fluid in the pump chamber.

As soon as the fluid in the primary piston pump 100 has reached system pressure, the outlet valve 106 is opened, and during the subsequent delivery-and-fill phase, the piston 104 continues moving upwards and supplies a flow of fluid to the secondary piston pump 101. During the delivery-and-fill phase, the piston 108 of the secondary piston pump 101 is moved downwards, as indicated by arrow 113. The fluid supplied by the primary piston pump 100 is used both for filling up the pump chamber of the secondary piston pump 101 and for maintaining a continuous flow of fluid at the outlet 109 of the secondary piston pump 101.

FIG. 2A shows the piston position p1 of the piston 104 as a function of time, and FIG. 2B, which is located right below, shows the piston position p2 of the piston 108 as a function of time. During the intake phase of the primary piston pump 100, the piston 104 performs a downward stroke 200, with fluid being drawn into the pump chamber of the primary piston pump 100. Simultaneously, the piston 108 of the secondary piston pump 101 performs an upward stroke 201 and dispenses a continuous flow of fluid at the outlet 109.

After a volume of fluid has been drawn into the pump chamber of the primary piston pump 100, the piston 104 performs an upward movement 202 to compress the fluid in the pump chamber to system pressure. This steep upward movement 202 will further on be referred to as a "compression jump".

At the point of time 203, the outlet valve 106 is opened, and during the delivery-and-fill phase 204, the piston 104 continues its upward stroke 205 and supplies a flow of fluid to the secondary piston pump 101. Simultaneously, the piston 108 of the secondary piston pump 101 performs a downward stroke 206 to draw in the fluid supplied by the primary piston pump 100.

Then, the entire pump cycle is repeated. The piston 104 of the primary piston pump 100 performs a downward stroke 207 to draw in fluid, and the piston 108 of the secondary piston pump 101 performs an upward stroke 208 to deliver fluid at the outlet 109.

During the delivery-and-fill phase 204, fluid is supplied to the secondary piston pump 101 at a flow rate of about 5 to 20 ml/min. As a consequence of this large delivery- and fill rate, the time period needed for refilling the secondary piston pump 101 can be kept quite short. In the example shown in FIGS. 2A and 2B, the delivery-and-fill phase 204 only extends over a small portion of the pump cycle 209. In state of the art pumping systems, the delivery-and-fill phase may extend over less than 10% of the pump cycle.

However, the stability and precision of the flow obtained at the pump system's outlet may be impaired by temperature variations of the fluid supplied by the primary piston pump 100. These temperature variations give rise to corresponding volumetric variations of the fluid contained in the pump system.

Figure 3:
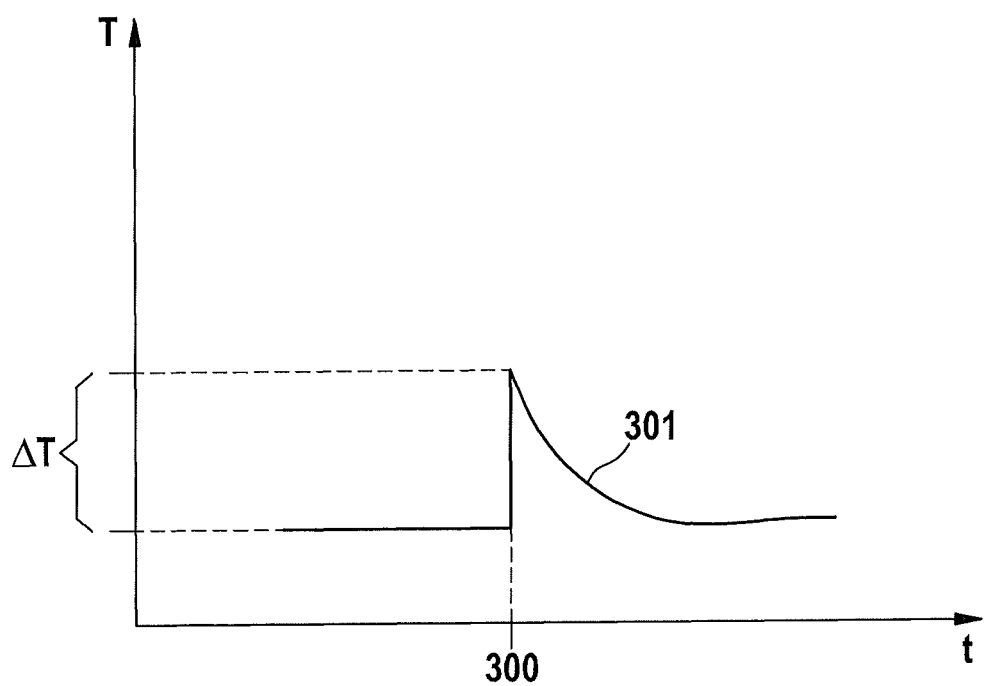
FIG. 3 shows temperature variations of the fluid in the pump system as a function of time.

In FIG. 3, the temperature variations of the fluid contained in the primary piston pump 100 are depicted as a function of time. At a point of time 300, the piston 104 of the primary piston pump 100 performs a compression jump to compress the fluid contained in the pump chamber to system pressure. Due to the compression, the fluid contained in the primary piston pump 100 is heated up, and a temperature increase $\Delta T$ is observed. Subsequently, when the primary piston pump 100 starts delivering fluid to the secondary piston pump 101, the heat generated during the compression phase dissipates, whereby different heat dissipation processes may occur simultaneously. For example, a first amount of heat $\Delta Q_1$ may dissipate via the walls of the primary piston pump 100, and a second amount of heat $\Delta Q_2$ may dissipate via the walls of the fluid conduit connecting the primary piston pump 100 and the secondary piston pump 101. In general, each of the various heat dissipation processes has a characteristic time constant, and each of the various heat dissipation processes contributes to the temperature relaxation of the fluid. Hence, the observed temperature relaxation 301 of the fluid is obtained as a superposition of various different heat dissipation processes having different characteristic time constants.

The temperature increase $\Delta T$ during the compression phase leads to a corresponding thermal expansion $\Delta V$ of the fluid contained in the pump chamber. Then, the subsequent temperature relaxation 301 causes a corresponding thermal contraction of the fluid. To obtain a precise flow of fluid at the outlet 109 of the pump system, thermal expansion and thermal contraction caused by temperature variations have to be compensated for by superposing corrective movements onto the piston movements of at least one of the pump system's pistons.

However, due to the liquid-specific extent of the heat generated, and due to the various different heat dissipation processes, it is difficult to come up with an exact model for compensation of the temperature relaxation 301. Furthermore, the temperature relaxation 301 strongly depends on the total volume of fluid contained in the primary piston pump 100, and therefore, the actual position of the piston 104 has to be taken into account when determining a suitable correction for the piston 104. In general, it is quite easy to compensate for the thermal expansion $\Delta V$ during the compression phase, but it is hard to come up with an accurate model of the various different heat dissipation processes. A further problem is that the temperature of the fluid supplied by the primary piston pump 100 differs from the temperature of the fluid in the secondary piston pump 101, which may lead to further flow disturbances when the two fluids mix in the pump chamber of the secondary piston pump 101.

According to embodiments of the present invention, a heat exchanger is fluidically coupled into the flow path connecting the primary piston pump and the secondary piston pump. Hence, fluid supplied by the primary piston pump has to pass through the heat exchanger before being provided to the secondary piston pump.

Figure 4:
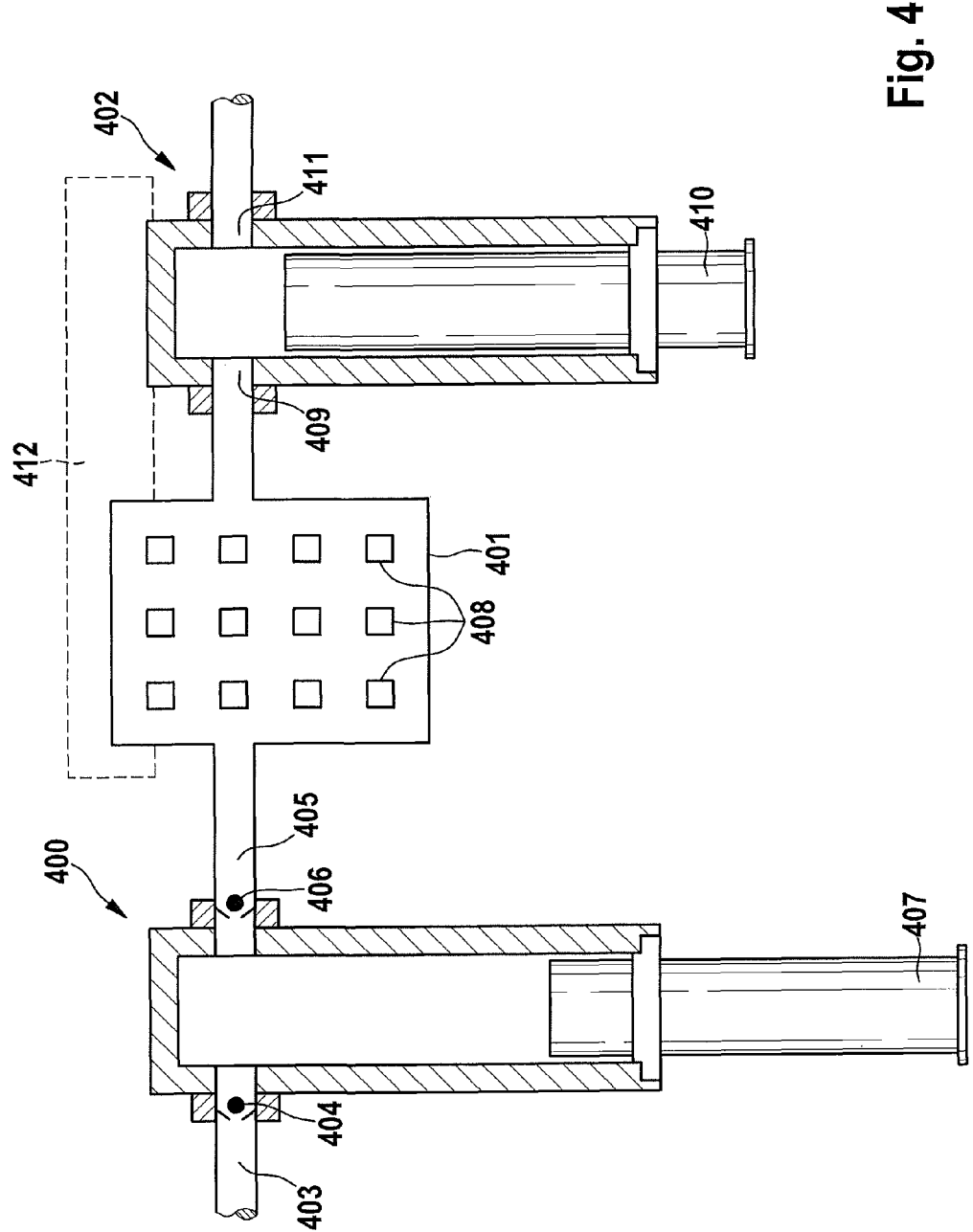
FIG. 4 shows a pump system according to an embodiment of the present invention, with a heat exchanger being included in the flow path between the primary piston pump and the secondary piston pump.

FIG. 4 shows an embodiment of the present invention comprising a primary piston pump 400, a heat exchanger 401 and a secondary piston pump 402. The primary piston pump 400 comprises an inlet 403 with an inlet valve 404, an outlet 405 with an outlet valve 406, and a piston 407 that reciprocates in the pump chamber of the primary piston pump 400. The outlet 405 of the primary piston pump 400 is fluidically coupled with an inlet of the heat exchanger 401. The heat exchanger 401 is kept at a predefined temperature. For this purpose, the heat exchanger 401 may e.g. be thermally coupled with a heat reservoir. In order to improve thermal contact between the heat exchanger 401 and the fluid passing through the heat exchanger 401, the heat exchanger 401 may e.g. comprise a plurality of heat exchanging elements 408 arranged in the heat exchanger's interior. The heat exchanging elements 408 may for example be realized as beads made of stainless steel. Flow stream patterns may be implemented by the heat exchanging elements 408 to intensify the thermal contact of liquid to the heat exchanger.

The outlet of the heat exchanger 401 is fluidically coupled with an inlet 409 of the secondary piston pump 402. The secondary piston pump 402 comprises a piston 410 reciprocating in the pump chamber of the secondary piston pump 402, and an outlet 411. At the outlet 411 of the secondary piston pump 402, a continuous flow of fluid is obtained.

When the fluid supplied by the primary piston pump 400 passes through the heat exchanger 401, the fluid's temperature is driven towards the heat exchanger's temperature. Hence, by arranging a heat exchanger 401 between the outlet 406 of the primary piston pump 400 and the inlet 409 of the secondary piston pump 402, a well-defined temperature relaxation process of the fluid passing through the heat exchanger 401 is performed. Instead of the complicated temperature relaxation 301 shown in FIG. 3, which depends on a multitude of different time constants, embodiments of the present invention provide for a temperature relaxation process that is mainly enforced by the presence of a heat exchanger 401. Temperature relaxation is controlled by the flow rate of the fluid supplied by the primary piston pump 400 during the delivery-and-fill phase. Hence, the temperature relaxation behavior is accurately known in advance, and therefore, the volumetric effects related to the fluid's temperature variations can be compensated for in a simple manner, e.g. by superposing suitable corrective movements onto the piston movements of at least one of the primary piston pump 400 and the secondary piston pump 402.

In most cases, the fluid that has been heated up during the compression phase is cooled down when passing through the heat exchanger 401. However, it may as well be possible that a fluid supplied by the primary piston pump 400 is warmed up when passing through the heat exchanger 401. Also in this case, the fluid passing through the heat exchanger 401 is brought to a predefined temperature. The superposed corrective movement may assume both polarities.

According to a preferred embodiment, the heat exchanger 401 is kept at the same temperature as the secondary piston pump 402, and therefore, fluid passing through the heat exchanger 401 is substantially brought to the temperature of the secondary piston pump 402. In order to keep both the heat exchanger 401 and the secondary piston pump 402 at the same temperature, the heat exchanger 401 may e.g. be thermally coupled with the secondary piston pump 402. In this embodiment, the temperature of the fluid supplied to the secondary piston pump 402 is the same as the temperature of the secondary piston pump 402 itself, and for this reason, the fluid supplied to the secondary piston pump 402 during the delivery-and-fill phase does not cause any thermal disturbances. Accordingly, a stable and continuous flow of fluid is obtained at the outlet 411.

According to a preferred embodiment, both the heat exchanger 401 and the secondary piston pump 402 are thermally coupled with a common heat reservoir 412, said common heat reservoir 412 being indicated with dashed lines. The common heat reservoir 412 is adapted for keeping both the heat exchanger 401 and the secondary piston pump 402 at the same temperature, which may be controllable.

The compression of the fluid contained in the primary piston pump 400 and the subsequent temperature relaxation of the fluid when passing through the heat exchanger 401 lead to a corresponding thermal expansion or contraction of the fluid in the pumping system. In order to obtain a precisely metered flow of fluid at the outlet 411, it is necessary to impose corrections onto the regular movement of at least one of the pistons 407 and 410. In the embodiments described in the following, corrections will solely be imposed onto the piston movement of the primary piston pump 400.

Figure 5A:
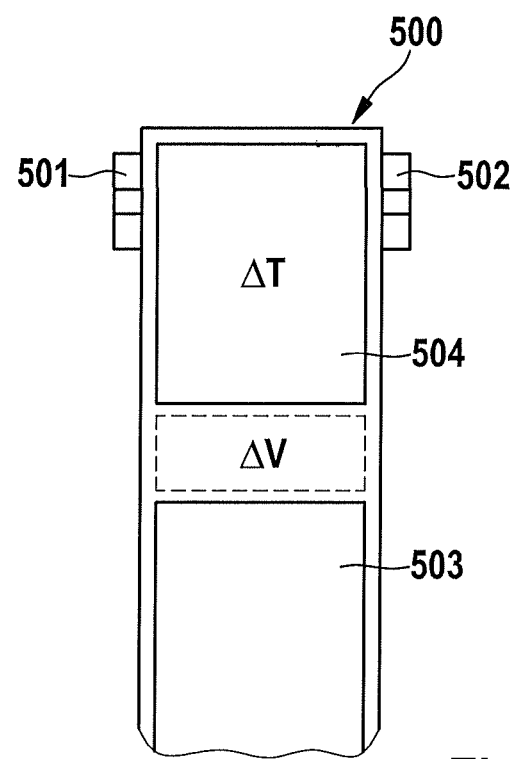
FIG. 5 illustrates a first corrective movement and a second corrective movement, which are superimposed onto the piston movement of the primary piston pump.

FIG. 5A illustrates how a thermal expansion of the fluid in the pump chamber that occurs during the compression phase is compensated for. In FIG. 5A, the primary piston pump 500 is depicted. During the compression phase, both the inlet valve 501 and the outlet valve 502 of the primary piston pump 500 are shut, and the piston 503 performs a compression jump to compress the volume of fluid 504 from atmospheric pressure to a system pressure of several hundred or even more than thousand bar.

During the compression jump, the volume of fluid 504 is heated up, and the temperature of the volume of fluid 504 is increased by $\Delta T$. The temperature increase $\Delta T$ leads to a corresponding volumetric expansion $\Delta V$ of the volume of fluid 504.

In order to compensate for the thermal expansion $\Delta V$ of the volume of fluid 504 during the compression phase, the compression jump performed by the piston 503 is reduced in accordance with the thermal expansion $\Delta V$. Instead of performing a regular compression jump, the piston 503 only performs a reduced compression jump, to take the additional thermal expansion $\Delta V$ into account.

Figure 6A:
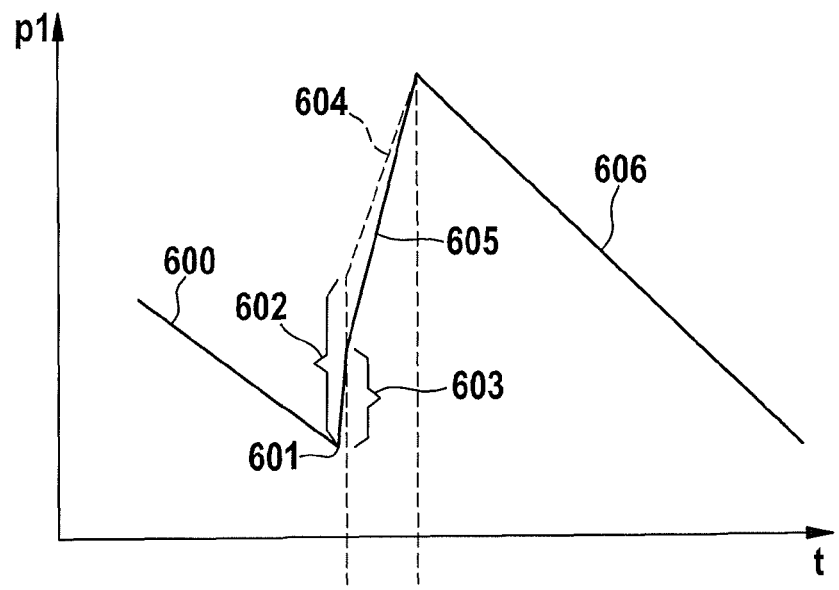
FIG. 6 shows corrected piston movements of the primary piston pump and the secondary piston pump after said corrective movements have been applied.

The corrective movements superimposed onto the regular movement of the primary piston pump's piston 503 are further illustrated in FIG. 6A. Below FIG. 6A, the corresponding piston movement of the secondary piston pump's piston is shown, which is not subjected to any corrections. From FIG. 6A, it can be seen that the piston 503 first performs a downward stroke 600 to draw in fluid. Then, at the point 601, the piston 503 starts moving in the upward direction and compresses the volume of fluid 504 in the pump chamber to system pressure. To correct for the thermal expansion of the volume of fluid 504, the piston 503 does not perform a regular compression jump 602, but a reduced compression jump 603, with the difference between the regular compression jump 602 and the reduced compression jump 603 being equal to the thermal expansion $\Delta V$ of the volume of fluid 504 during the compression phase.

Figure 5B:
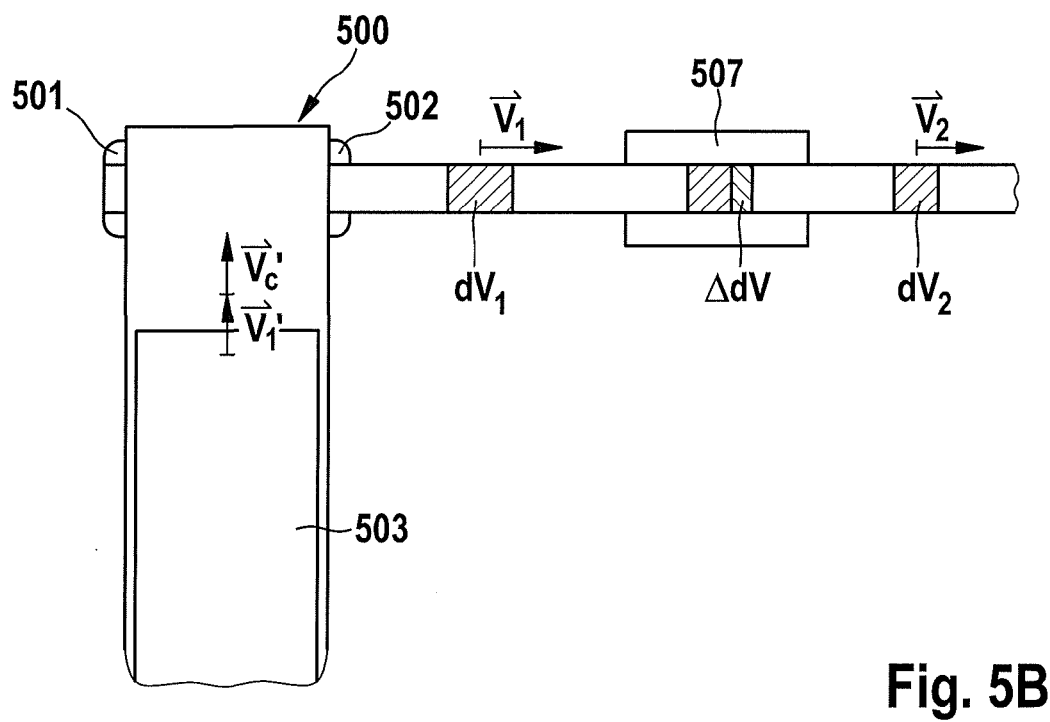

After the reduced compression jump 603 has been performed, the fluid contained in the primary piston pump 500 is at system pressure. Now, as shown in FIG. 5B, the piston 503 continues its upward movement, the outlet valve 502 is opened, and a flow of fluid is dispensed at the outlet 505 of the primary piston pump 500. The flow of fluid is supplied, via a fluid conduit 506 and a heat exchanger 507, to the secondary piston pump, and with the primary piston moving in fast delivery-and-fill mode, the secondary piston pump's pump chamber is filled with the fluid supplied by the primary piston pump 500.

In order to track the volumetric effects related to temperature variations, a certain quantity of fluid is observed as it passes along the fluid conduit 506 and through the heat exchanger 507. Before reaching the heat exchanger 507 with only minor change in temperature, the quantity of fluid occupies a volume $dV_1$. In case the quantity of fluid is cooled down in the heat exchanger 507, the temperature decrease $\Delta T_{HE}$ leads to a corresponding thermal contraction of the volume of fluid $dV_1$. Therefore, after having passed through the heat exchanger 507, the volume $dV_2$ of the observed volumetric quantity of fluid is considerably smaller than the volume of fluid $dV_1$. The relationship between the volume $dV_1$ before reaching the heat exchanger 507 and the volume $dV_2$ after having passed through the heat exchanger can be expressed as follows:

$$dV_1 - \Delta dV = dV_2 \quad (1)$$

wherein $\Delta dV$ denotes the thermal contraction of the volume of fluid $dV_1$. The thermal contraction $\Delta dV$ can be expressed in terms of the fluid's thermal expansion coefficient $\square$, the temperature decrease $\Delta T_{HE}$ and the volume $dV_1$ as follows:

$$\Delta dV = \square \cdot \Delta T_{HE} \cdot dV_1 \quad (2)$$

Next, it is assumed that an infinitesimal time interval dt is needed for the volume $dV_1$ to pass by. Correspondingly, the same infinitesimal time interval dt is needed for the volume $dV_2$ to pass by. Hence, the volume per unit time $dV_1/dt$ before arriving at the heat exchanger 507 and the volume per unit time $dV_2/dt$ after passing through the heat exchanger can be related to one another as follows:

$$(1 - \square \cdot \Delta T_{HE}) \cdot dV_1/dt = dV_2/dt \quad (3)$$

The volume per unit time $dV_1/dt$ before arriving at the heat exchanger 507 can be expressed in terms of the fluid's velocity $v_1$:

$$dV_1/dt = A \cdot v_1 \quad (4)$$

with A denoting a cross section of the fluid conduit 506. In the same way, the volume per unit time $dV_2/dt$ of the fluid after having passed through the heat exchanger 507 can be expressed in terms of the fluid velocity $v_2$ as follows:

$$dV_2/dt = A \cdot v_2 \quad (5)$$

with A denoting the cross section of the fluid conduit 506. By plugging these relations into the above formula (3), a relationship between the velocity $v_1$ of the volume $dV_1$ and the velocity $v_2$ of the volume $dV_2$ is obtained:

$$(v_1 - \square \cdot \Delta T_{HE} \cdot v_1) = v_2 \quad (6)$$

and with $$v_C = \square \cdot \Delta T_{HE} \cdot v_1 \quad (7)$$

this relation between the velocity $v_1$ and the velocity $v_2$ can be simplified to:

$$v_1 - v_C = v_2 \quad (8)$$

Hence, when a volume $dV_1$ passes through the heat exchanger 507, it experiences a thermal contraction, and as a consequence, the velocity $v_1$ of the volume $dV_1$ is reduced. At the outlet of the heat exchanger 507, a volume $dV_2$ travelling with a reduced speed $v_2$ is obtained. By cooling down the volume $dV_1$ passing through the heat exchanger 507, both the volume itself and the travelling velocity of said volume are reduced, which is a consequence of the thermal contraction experienced when the volume of fluid passes through the heat exchanger.

To compensate for the decrease of velocity experienced by a volume of fluid when passing through the heat exchanger, an additional forward velocity is superimposed, as a corrective movement, onto the forward movement of the piston 503. The actual velocity of the piston 503 is obtained as a sum of the regular forward velocity $v_1'$ and an additional velocity $v_C'$. For example, in case the fluid passing through the heat exchanger 507 is cooled down, an additional forward velocity $v_C'$ is imposed, as a corrective movement, onto the regular piston movement. In this case, both the velocity $v_1$ of the volume $dV_1$ and the velocity $v_2$ of the volume $dV_2$ are increased. The additional forward velocity $v_C'$ can be chosen such that a desired travelling velocity $v_2$ of the volume $dV_2$ is obtained.

In FIG. 6A, an example of a corrective movement applied to the piston movement of the primary piston pump during the delivery-and-fill phase is illustrated. Instead of a regular piston movement 604 (indicated with dashed lines), which starts at the end of the regular compression jump 602, a corrected piston movement 605 is carried out, which starts at the end of the corrected compression jump 603. In FIG. 6A, it can be seen that the slope of the corrected piston movement 605 is considerably steeper than the slope of the regular piston movement 604. The increased slope of the corrected piston movement 605 corresponds to adding an additional forward velocity $v_C'$ to the regular forward velocity $v_1'$ of the piston 503 during the piston's upward stroke.

When the primary piston pump's delivery phase is completed, the piston 503 performs a downward movement and draws in fluid at atmospheric pressure. This intake phase 606 is also indicated in FIG. 6A.

Figure 6B:
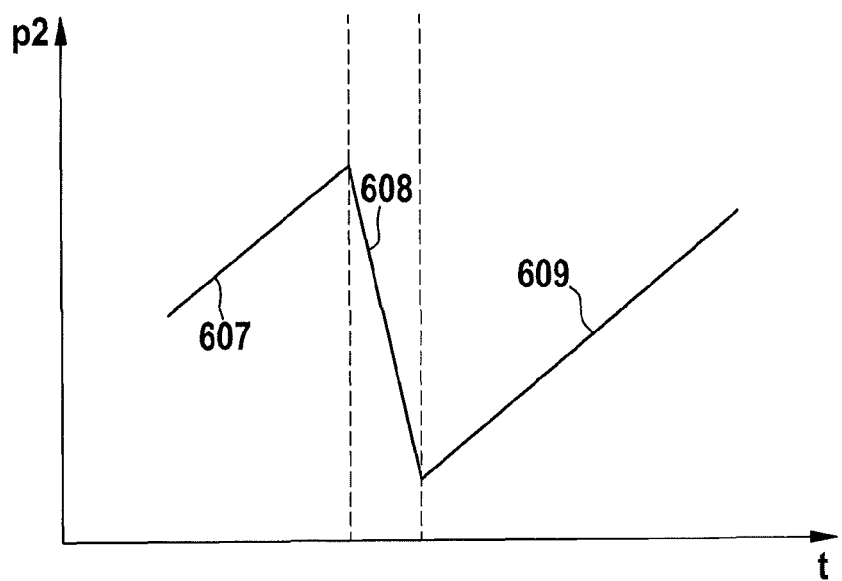

In FIG. 6B, which is located below FIG. 6A, the piston movement of the secondary piston pump is indicated as a function of time. During the primary piston pump's intake phase 600, the secondary piston pump's piston performs an upward stroke 607 and dispenses a continuous flow of fluid at its outlet. Then, during the delivery-and-fill phase 608, the secondary piston pump's piston moves in the downward direction, and the pump volume of the secondary piston pump is filled up with the flow of fluid supplied by the primary piston pump. During the delivery-and-fill phase 608, only a fraction of the flow supplied by the primary piston pump is used for maintaining a continuous flow of fluid at the secondary piston pump's outlet. After the pump chamber of the secondary piston pump has been filled up, the secondary piston pump's piston performs an upward stroke 609 and again dispenses a flow of fluid at its outlet.

Hence, to correct for thermal effects, two different corrective movements are applied to the regular piston movement of the primary piston pump 500: As a first corrective movement, the length of the compression jump is reduced in accordance with the thermal expansion $\Delta V$ of the fluid contained in the pump chamber. Then, as a second corrective movement, an additional velocity is superposed onto the regular forward movement of the primary piston pump's piston 503 during the delivery phase. Said additional velocity $v_C'$ compensates for the thermal contraction imposed by the heat exchanger 507.

So far, it has been assumed that the flow of fluid is cooled down when passing through the heat exchanger 507. However, the heat exchanger 507 may as well be configured to warm up the fluid before the fluid is supplied to the secondary piston pump. In case the fluid is warmed up when passing through the heat exchanger 507, it may be necessary to apply an additional backward velocity as a corrective movement onto the regular piston movement.

Figure 7A:
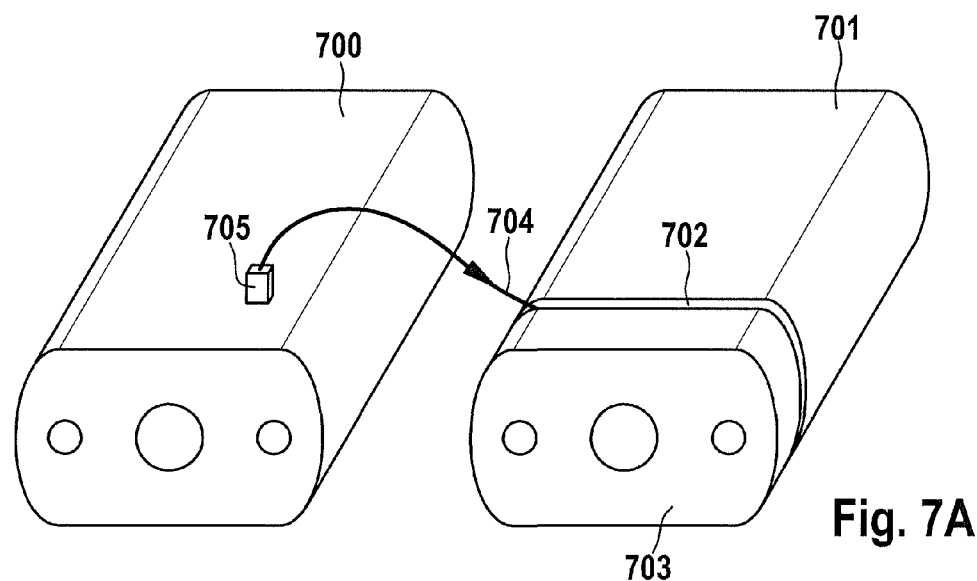
FIG. 7 shows an embodiment of the present invention in which the heat exchanger is realized as a planar structure adapted for being mounted to the secondary piston pump.
Figure 7B:
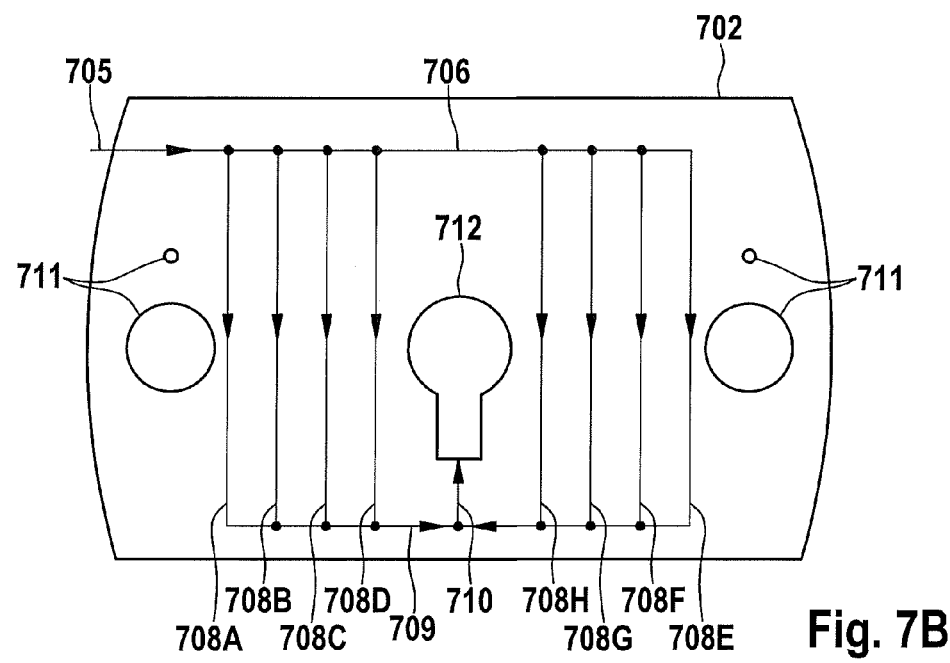

In FIGS. 7A and 7B, another embodiment of the present invention is shown, in which the heat exchanger is realized as a planar structure that is mounted onto the secondary piston pump, with the planar structure comprising a plurality of fluid channels. FIG. 7A gives an overview of the set-up, which comprises a primary piston pump 700 fluidically connected in series with a secondary piston pump 701. A planar heat exchanger 702 is mounted to the front face of the secondary piston pump 701. For example, the heat exchanger 702 may e.g. be fixed to the front face of the secondary piston pump 701 by means of a contact block 703 that is screwed onto the secondary piston pump 701. Thus, an excellent thermal contact is established between the planar heat exchanger 702, which is preferably made of metal, and the secondary piston pump 701. The heat exchanger 702 is substantially kept at the temperature of the secondary piston pump 701.

The inlet 704 of the heat exchanger 702 is fluidically coupled with the outlet 705 of the primary piston pump 700. The outlet of the heat exchanger 702 (which is not shown in FIG. 7A) is fluidically coupled with the inlet of the secondary piston pump 701. Hence, fluid supplied by the primary piston pump 700 is conveyed through the heat exchanger 702 before being supplied to the secondary piston pump 701. The heat exchanger 702 is adapted for bringing fluid supplied by the primary piston pump 700 to the secondary piston pump's temperature before said fluid is supplied to the secondary piston pump 701.

FIG. 7B gives a more detailed view of the inner routing of fluidic lines inside of the heat exchanger 702. The heat exchanger 702 may e.g. be implemented as a planar multilayer structure made of two or more bonded metal sheets. The heat exchanger 702 comprises an input channel 706 that is fluidically coupled with an inlet 707 of the heat exchanger 702. Fluid supplied to the input channel 706 is distributed to a plurality of transfer channels 708A to 708H. When passing through the transfer channels, the temperature of the fluid is brought to the temperature of the heat exchanger 702. After the fluid has passed through the transfer channels 708A to 708H, it is collected by the output channel 709 and dispensed at the outlet 710 of the heat exchanger 702. The outlet 710 is fluidically coupled with the inlet of the secondary piston pump 701.

In order to mount the heat exchanger 702 onto the secondary piston pump 701, the heat exchanger 702 may comprise a plurality of holes 711 and a cut-out 712. For example, the heat exchanger 702 may be screwed onto the front face of the secondary piston pump 701. Thus, thermal contact is established between the heat exchanger 702 and the secondary piston pump 701.

The invention claimed is:

1. A pump unit comprising:
a primary piston pump,
a secondary piston pump,
a flow path fluidically connecting in series the primary piston pump and the secondary piston pump, wherein:
the pump unit is configured for executing a duty cycle comprising a delivery-and-fill phase, in which the primary piston pump supplies a flow of liquid to the secondary piston pump, and during the delivery-and-fill phase, the flow of liquid supplied by the primary piston pump is partly used for filling up the secondary piston pump and partly used for maintaining continuous flow of liquid dispensed at an outlet of the secondary piston pump,
the flow path comprises a heat exchanger, wherein liquid supplied by the primary piston pump passes through the heat exchanger before being supplied to the secondary piston pump, and
the heat exchanger is configured for reducing a temperature difference between a temperature of liquid supplied to the heat exchanger and a temperature of the secondary piston pump influenced by flow rates of liquid supplied by the primary piston pump, and enforced by the heat exchanger, during the delivery-and-fill phase, in that the heat exchanger is kept at a temperature of the secondary piston pump, so that after having passed the heat exchanger, liquid supplied to the secondary piston pump during the delivery-and-fill phase has substantially the same temperature as the temperature of the secondary piston pump,
and further comprising one or more of the following:
a thermostatic heating element configured to keep both the heat exchanger and the secondary piston pump at a predefined temperature;
the heat exchanger comprises a heat reservoir and one or more capillaries in thermal contact with the heat reservoir;
a control unit configured to superpose at least one corrective movement to at least one of the primary piston pump and secondary piston pump so as to compensate for volumetric effects that are due to temperature variations of the liquid;
a common heat reservoir thermally coupling the heat exchanger and the secondary piston pump;

the pump unit being configured to execute the duty cycle such that the delivery-and-fill phase extends over less than 10% of the duty cycle; or the heat exchanger comprising a pattern of heat exchange elements configured to intensify the thermal contact of liquid to the heat exchanger.

2. The pump unit of claim 1, wherein the heat exchanger is adapted for at least one of:

substantially bringing the liquid supplied by the primary piston pump to a predefined temperature before said liquid is supplied to the secondary piston pump;

substantially bringing the liquid supplied by the primary piston pump to the secondary piston pump's temperature.

3. A liquid separation system for separating compounds of a sample liquid in a mobile phase, the liquid separation system comprising:

a mobile phase drive adapted to drive the mobile phase through the liquid separation system, said mobile phase drive comprising a pump unit according to claim 1, and a separation unit adapted for separating compounds of the sample liquid in the mobile phase.

4. The liquid separation system of claim 3, further comprising at least one of:

a sample injector adapted to introduce the sample liquid into the mobile phase;

a detector adapted to detect separated compounds of the sample liquid;

a collection unit adapted to collect separated compounds of the sample liquid;

a data processing unit adapted to process data received from the liquid separation system;

a degassing apparatus for degassing the mobile phase.

5. The pump unit of claim 1, wherein the heat exchanger is thermally coupled to the secondary piston pump.

6. The pump unit of claim 1, wherein the heat exchanger is mounted onto the secondary piston pump.

7. The pump unit of claim 1, wherein the duty cycle comprises an intake phase executed by the primary piston pump, followed by a compression jump executed by the primary piston pump, followed by the delivery-and-fill phase, and wherein the compression jump and the delivery-and-fill phase cause temperature variations in the fluid supplied by the primary piston pump.

8. The pump unit of claim 7, wherein the duty cycle comprises a dispensing phase executed by the secondary piston pump during the intake phase executed by the primary piston pump, followed by an intake phase executed by the secondary piston pump during the delivery-and-fill phase.

* * * * *